United States Patent
Lannfelt et al.

(10) Patent No.: US 8,809,506 B2
(45) Date of Patent: Aug. 19, 2014

(54) ANTIBODIES AND VACCINES FOR USE IN THERAPEUTIC AND DIAGNOSTIC METHODS FOR α-SYNUCLEIN-RELATED DISORDERS

(75) Inventors: Lars Lannfelt, Stockholm (SE); Joakim Bergström, Uppsala (SE); Martin Ingelsson, Uppsala (SE); Pär Gellerfors, Lindingö (SE)

(73) Assignee: BioArctic Neuroscience AB, Stockholm (SE)

( * ) Notice: Subject to any disclaimer, the term of this patent is extended or adjusted under 35 U.S.C. 154(b) by 237 days.

(21) Appl. No.: 12/990,226

(22) PCT Filed: Apr. 28, 2009

(86) PCT No.: PCT/IB2009/051731
§ 371 (c)(1),
(2), (4) Date: Oct. 29, 2010

(87) PCT Pub. No.: WO2009/133521
PCT Pub. Date: Nov. 5, 2009

(65) Prior Publication Data
US 2011/0052498 A1 Mar. 3, 2011

Related U.S. Application Data

(60) Provisional application No. 61/048,865, filed on Apr. 29, 2008.

(51) Int. Cl.
*A61K 39/395* (2006.01)
*C07K 16/18* (2006.01)
*G01N 33/567* (2006.01)
*A61K 38/17* (2006.01)
*G01N 33/68* (2006.01)

(52) U.S. Cl.
CPC ........ *G01N 33/6896* (2013.01); *A61K 38/1709* (2013.01); *C07K 16/18* (2013.01); *G01N 2333/4709* (2013.01); *Y10S 530/839* (2013.01)
USPC .................... 530/388.1; 530/839; 424/139.1; 435/7.21

(58) Field of Classification Search
None
See application file for complete search history.

(56) References Cited

U.S. PATENT DOCUMENTS

| | | |
|---|---|---|
| 7,179,463 B2 | 2/2007 | Lannfelt et al. |
| 7,700,719 B2 | 4/2010 | Lannfelt et al. |
| 2002/0162129 A1 | 10/2002 | Lannfelt et al. |
| 2005/0203010 A1 | 9/2005 | Kim |
| 2006/0018918 A1 | 1/2006 | Chang |
| 2006/0058233 A1 | 3/2006 | Schenk et al. |
| 2006/0259986 A1 | 11/2006 | Chilcote et al. |
| 2007/0248606 A1 | 10/2007 | Lannfelt et al. |
| 2008/0014194 A1 | 1/2008 | Schenk et al. |
| 2008/0181902 A1 | 7/2008 | Lannfelt et al. |
| 2009/0155246 A1 | 6/2009 | Gellerfors et al. |
| 2009/0258009 A1 | 10/2009 | Gellerfors et al. |

FOREIGN PATENT DOCUMENTS

| | | |
|---|---|---|
| WO | 00/02053 A2 | 1/2000 |
| WO | 02/03911 A2 | 1/2002 |
| WO | 2004/041067 A2 | 5/2004 |
| WO | 2005/013889 A2 | 2/2005 |
| WO | 2005/047860 A2 | 5/2005 |
| WO | 2006/020581 A2 | 2/2006 |
| WO | 2006/045037 A2 | 4/2006 |
| WO | 2007/089862 A2 | 8/2007 |

OTHER PUBLICATIONS

Baba et al., Am J Pathology, 152(4):879-884, Apr. 1998.*
Reichmann et al., Nature, 332: 323-327, 1988.*
Sigma-Aldrich product information sheet for Tween 20, dated May 2006.*
Bosco et al., Nature Chemical Biology, 2(5): 249-253, published online Mar. 26, 2006.*
Milne et al., J Bacteriol. 92(3):543, 1966.*
Cole et al, J Biol Chem., 280(10):9678-9690, Dec. 2004.*
Lindgren and Harramrström, FEBS J., 277(6):1380-8, Mar. 2010.*
Zhou and Przedborski, Biochimica et Biophysica Acta, 1792: 634-642, epublished Sep. 12, 2008.*
Qin et al, The Journal of Biological Chemistry, 282(8):5862-5870 (Feb. 23, 2007).
Pountney et al, Neurotoxicity Research, 7(1-2):59-67 (2005).
Trostchansky et al, The Biochemical Journal, 393(Pt 1):343-349 (2006).
Lee et al, Journal of Neurochemistry, 76(4):998-1009 (2001).
Davidson et al, The Journal of Biological Chemistry, 273(16):9443-9449 (1998).
Shtilerman et al, Biochemistry, 41(12):3855-3860 (2002).
Nasstrom et al, Biochemical and Biophysical Research Communications, 378(4):872-876 (Jan. 23, 2009).
Beyer et al, Current Medicinal Chemistry, 15(26):2748-2759 (Nov. 2008).
Nasstrom et al, Alzheimer's & Dementia: The Journal of the Alzheimer's Association, 4(4):T754 (Jul. 1, 2008).
Bergstrom et al, Alzheimer's & Dementia: The Journal of the Alzheimer's Association, 4(4):T435 (Jul. 1, 2008).

(Continued)

*Primary Examiner* — Daniel E Kolker
*Assistant Examiner* — Stacey N MacFarlane
(74) *Attorney, Agent, or Firm* — Porter Wright Morris & Arthur LLP

(57) ABSTRACT

A vaccine for delaying an onset of or for treatment of an α-synuclein-related disorder in an individual comprises a therapeutically effective amount of isolated stabilized soluble α-synuclein oligomer having a lower formation rate to a non-soluble aggregated form than a non-stabilized oligomer of the α-synuclein. An antibody for delaying an onset of or for treatment of an α-synuclein-related disorder in an individual binds soluble α-synuclein. Methods for delaying an onset of for treatment or for prevention of an α-synuclein-related disorder employ the vaccine or antibody. Methods of detecting α-synuclein oligomers employ the antibody.

44 Claims, 6 Drawing Sheets

(56) References Cited

OTHER PUBLICATIONS

Zhou et al, Molecular Therapy, Academic Press, 10(6):1023-1031 (2004).
Emadi et al, Biochemistry, 43(10):2871-2878 (2004).
McGuire-Zeiss et al, Molecular Therapy: The Journal of the American Society of Gene Therapy, 9(Supp. 1):S86 (2004).
McGuire-Zeiss et al, Biochemical and Biophysical Research Communications, 349(4):1198-1205 (2006).
Miller et al, Molecular Therapy, 12(3):394-401 (2005).
Lynch et al, Journal of Molecular Biology, 377(1):136-147 (2007).
Emadi et al, Journal of Molecular Biology, 368(4):1132-1144 (Apr. 17, 2007).
Nannenga et al, FEBS Letters, 582(4):517-522 (Jan. 28, 2008).
Papachroni et al, Journal of Neurochemistry, 101(3):749-756 (May 1, 2007).
Kostka et al, The Journal of Biological Chemistry, 283(16):10992-11003 (Apr. 18, 2008).
Wahlberg et al, Alzheimer's & Dementia: The Journal of the Alzheimer's Association, 4(4):T481-482 (Jul. 1, 2008).
Official Action dated Oct. 15, 2013 from corresponding JP 2011-506815 and an English translation thereof.

* cited by examiner

US 8,809,506 B2

ANTIBODIES AND VACCINES FOR USE IN THERAPEUTIC AND DIAGNOSTIC METHODS FOR α-SYNUCLEIN-RELATED DISORDERS

RELATED APPLICATIONS

The present application is a 371 of PCT/IB2009/051731 filed Apr. 28, 2009 and claims priority under 35 U.S.C. 119 of U.S. application Ser. No. 61/048,865 filed Apr. 29, 2008.

FIELD OF THE INVENTION

The present invention relates to antibodies and vaccines and their use in therapeutic and diagnostic methods for α-synuclein related disorders, i.e., α-synucleinopathies wherein accumulation of aggregated insoluble α-synuclein in the form of Lewy bodies and/or Lewy neurites are present in the brain. Such disorders include, but are not limited to, neurodegenerative disorders such as Parkinson's disease (PD), dementia with Lewy bodies (DLB), the Lewy body variant of Alzheimer's disease, multiple system atrophy and other neurodegenerative disorders with α-synuclein pathology.

More specifically, the invention relates to vaccines comprising isolated stabilized soluble α-synuclein oligomers having a lower formation rate to a non-soluble aggregated form than a non-stabilized oligomer of the α-synuclein. The stabilized soluble α-synuclein oligomer may be in the form of, for example, a larger oligomer, referred to as a protofibril. The invention also relates to antibodies which bind soluble α-synuclein.

The invention is also directed to methods of detecting α-synuclein, in vitro or in vivo, and to methods for delaying an onset of, treating, or preventing an α-synuclein-related disorder such as, but not limited to, Parkinson's disease, dementia with Lewy bodies, Lewy body variant of Alzheimer's disease, and multiple system atrophy. Both active immunization and passive methods are disclosed.

BACKGROUND OF THE INVENTION

Parkinson's disease (PD) and dementia with Lewy bodies (DLB) are the two most prevalent examples of neurodegenerative disorders with α-synuclein brain pathology.

PD is the most common movement disorder and is characterized by rigidity, hypokinesia, tremor and postural instability. PD is believed to affect approximately four to six million people worldwide.

DLB represents 5-15% of all dementia. In addition to forgetfulness and other dementing symptoms that often fluctuate, DLB patients typically suffer from recurrent falls and visual hallucinations.

Intraneuronal accumulation of α-synuclein either results in the formation of Lewy bodies, round 10-20 µm large eosinophilic hyaline inclusions, or Lewy neurites, elongated threadlike dystrophic axons and dendrites. In the PD brain, deposition of Lewy bodies and Lewy neurites are limited to neurons connecting striatum with substantia nigra. These cells are crucial for the execution of movement and postural functions, explaining the nature of PD symptoms. In the DLB brain, widespread depositions of Lewy bodies and Lewy neurites are found both in midbrain and cortical areas.

Alpha-synuclein is a protein which is mainly found intraneuronally. Within the neuron, α-synuclein is predominantly located presynaptically and it has therefore been speculated that it plays a role in the regulation of synaptic activity. Three main isoforms of α-synuclein have been identified, of which the longest and most common form comprises 140 amino acids.

In addition to α-synuclein, Lewy bodies consist of a wide range of molecules, one of which is 4-hydroxy-2-nonenal (HNE), an α,β-unsaturated hydroxyalkenal (Qin et al., 2007). It has been shown in vitro that HNE can modify α-synuclein and thereby facilitate α-synuclein oligomerization. In particular, HNE has been shown to increase and stabilize the formation of protofibrils, i.e. soluble larger oligomeric forms of α-synuclein (Qin et al., 2007). Similarly, the α,β-unsaturated alkenal 4-oxo-2-nonenal (ONE) has also been shown to modify α-synuclein and thereby induce α-synuclein oligomerization (Näsström et al. 2009).

HNE reacts and modifies side chains of cysteine, histidine and lysine, whereas ONE reacts and modifies side chains of cysteine, histidine, lysine and arginine. Both HNE and ONE substantially alter the structure and physical properties of these side chains. Hence, HNE and ONE can either react with the C-3 carbon or with the aldehyde group or by combinations thereof. Hence, HNE can covalently modify proteins, either inter- or intramolecularly.

Oxidative stress has been implicated in a number of neurodegenerative disorders characterized by the pathological accumulation of misfolded α-synuclein. Various reactive oxygen species can induce peroxidation of lipids such as cellular membranes or lipoproteins and also result in the generation of highly reactive aldehydes from poly-unsaturated fatty acids (Yoritaka et al., 1996).

Brain pathology indicative of Alzheimer's disease (AD), i.e. amyloid plaques and neurofibrillary tangles, are seen in approximately 50% of cases with DLB. It is unclear whether the existence of parallel pathologies implies two different diseases or represents a variant of each respective disorder. Sometimes the cases with such co-pathology are described as having a Lewy body variant of AD (Hansen et al., 1990).

Rare dominantly inherited forms of PD and DLB can be caused by point mutations or duplications of the α-synuclein gene. The pathogenic mutations A30P and A53T (Kruger et al., 1998) (Polymeropoulos et al., 1998) and duplication of the gene (Chartier-Harlin et al. 2004) have been described to cause familial PD, whereas one other α-synuclein mutation, E46K (Zarranz et al., 2004) as well as triplication of the α-synuclein gene (Singleton et al., 2003) have been reported to cause either PD or DLB.

The pathogenic consequences of the α-synuclein mutations are only partly understood. However, in vitro data have shown that the A30P and A53T mutations increase the rate of aggregation (Conway et al., 2000). A broad range of differently composed α-synuclein species are formed in the aggregation process, all of which may have different toxic properties. Apart from the neuropathological changes in α-synucleinopathies, levels of α-synuclein protein are generally increased in affected brain regions (Klucken et al., 2006).

There is a need for improved diagnostic tools and methods to identify a risk for and/or early stages of a neurodegenerative disease with α-synuclein pathology. Currently, there is no biochemical method to aid a clinician's diagnosis of a patient before a more advanced symptomatic disease stage is evident, when substantial damage to the brain has already occurred. The importance of accurate diagnostic assays will become even greater as new and early stage therapeutic possibilities emerge. Currently, only symptomatic treatment (e.g., by substituting the loss of active dopamine in the brain) is available for PD patients. For DLB, even less therapeutic options are available. Nevertheless, clinicians are frequently evaluating possible beneficial effects on DLB patients with the standard treatment for AD, i.e. cholinesterase inhibitors, but no substantial improvement can commonly be seen. None of the existing treatment strategies for α-synucleinopathies are directed against the respective underlying disease processes. In addition, there is also a need for monitoring disease progress and treatment effects.

SUMMARY OF THE INVENTION

Accordingly, it is an object of the present invention to provide antibodies and vaccines for use in therapeutic and/or diagnostic methods for α-synuclein related disorders, i.e., α-synucleinopathies wherein accumulation of aggregated insoluble α-synuclein in the form of Lewy bodies and/or Lewy neurites are present in the brain. Such disorders include, but are not limited to, one or more neurodegenerative disorders such as Parkinson's disease (PD), dementia with Lewy bodies (DLB), the Lewy body variant of Alzheimer's disease, multiple system atrophy and other neurodegenerative disorders with α-synuclein pathology.

In one embodiment, the invention is directed to a vaccine for delaying an onset of or for treatment of an α-synuclein-related disorder in an individual, wherein the vaccine comprises a therapeutically effective amount of isolated stabilized soluble α-synuclein oligomer having a lower formation rate to a non-soluble aggregated form than a non-stabilized oligomer of the α-synuclein. In another embodiment, the invention is directed to a method for delaying an onset of or for treatment of an α-synuclein-related disorder in an individual, comprising administering to the individual a vaccine according to the invention. In a further embodiment, the invention is directed to use of a vaccine according to the invention for producing antibody against soluble α-synuclein.

In another embodiment, the invention is directed to an antibody for delaying an onset of or for treatment of an α-synuclein-related disorder in an individual, wherein the antibody binds soluble α-synuclein. In another embodiment, the invention is directed to a method for delaying an onset of or for treatment of an α-synuclein-related disorder in an individual, comprising administering to the individual an antibody according to the invention.

In another embodiment, the invention is directed to a method of producing an antibody for delaying an onset of or for treatment of an α-synuclein-related disorder in an individual, wherein the antibody or fragment thereof binds soluble α-synuclein. The method comprises administering an antigen to a non-human animal; and collecting antibody formed against the antigen, the antigen comprising stabilized soluble α-synuclein oligomer having a lower formation rate to a non-soluble aggregated form than a non-stabilized oligomer of the α-synuclein.

In yet a further embodiment, the invention is directed to antibody compositions and vaccine compositions, comprising an antibody or a vaccine, respectively, according to the invention and one or more excipients selected from the group consisting of antibacterial agents, adjuvants, buffers, salts, pH-regulators, detergents, and any combination thereof, that are pharmaceutically acceptable for human and/or veterinary use.

In additional embodiments, the invention is directed to detection methods. In one embodiment, a method of detecting α-synuclein oligomers in vitro comprises adding an antibody according to the invention to a biological sample comprising or suspected of comprising soluble α-synuclein; and detecting and measuring a concentration of any complex formed between the antibody and soluble α-synuclein. In another embodiment, a method of detecting α-synuclein oligomers in vivo comprises administering to an individual suspected of carrying soluble α-synuclein an antibody according to the invention, the antibody being labelled with a detectable marker; and detecting the presence of any complex formed between the antibody and soluble α-synuclein by detection of the marker.

The vaccines, antibodies, and methods of the invention are advantageous for diagnostic and therapeutic techniques directed to α-synuclein-related disorders. Additional embodiments and aspects of the invention are set forth in the Detailed Description, and additional advantages of the invention will be apparent therefrom.

BRIEF DESCRIPTION OF THE DRAWINGS

The present invention is further described with reference to the drawings, in which.

DETAILED DESCRIPTION OF THE INVENTION

Figure 1:
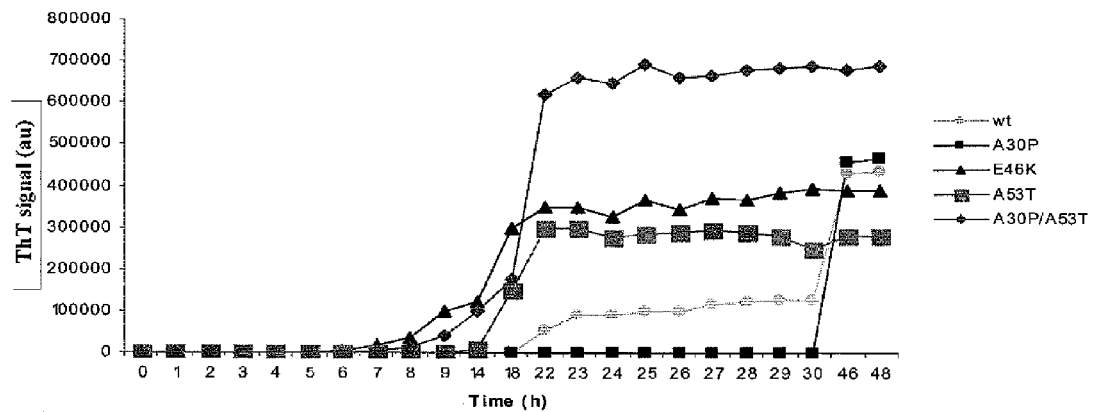
FIG. 1 shows a comparison of the aggregation rates of the wild-type and mutated forms of α-synuclein as measured by a ThT (Thioflavin T) assay, as described in Example 1. Thioflavin T is a reagent that binds to aggregated forms of α-synuclein, i.e. to β-sheet structures. The different α-synuclein species describe the following aggregation propensity: E46K>A30P/A53T>A53T>wt (wild type)>A30P. The fastest aggregating α-synuclein species is thus E46K, whereas the A30P mutant exhibits an aggregation rate even slower than that for wild-type α-synuclein.

The present invention provides antibodies (passive immunization) and vaccines (active immunization) for use in various methods for diagnosing and combating (including delaying the onset of, treatment of and/or prevention of) α-synuclein-related disorders such as one or more of Parkinson's disease (PD), dementia with Lewy bodies (DLB), the Lewy body variant of Alzheimer's disease, multiple system atrophy (MSA) and other neurodegenerative disorders with α-synuclein pathology. In addition, the antibodies and vaccines may be used in delaying the onset of, treatment and/or prevention of other neurodegenerative disorders such as Alzheimer's disease, Down's syndrome, amyotrophic lateral sclerosis, frontotemporal dementia, Huntington's disease, prion disease, Creutzfeldt Jakob's disease, Gerstmann-Sträussler-Scheinker syndrome, Kuru, fatal familial insomnia, cerebrovascular amyloidosis, glaucoma, age-related macular degeneration, psychiatric syndromes, schizophrenia and/or schizophrenia-like disorders. The antibodies and vaccines may also be used in detection methods for, inter alia, diagnostic, monitoring or therapy purposes.

The major pathology in α-synucleinopathies is intracellular, which poses a challenge to the immune therapeutic approach. However, it is likely that a fraction of actively induced or passively administered antibodies can bind their target antigens also intraneuronally. Moreover, the identification of α-synuclein in both plasma and cerebrospinal fluid (El-Agnaf et al., 2006) illustrates that the protein is not exclusively found within neurons. Without being bound by theory, reducing extracellular α-synuclein may shift the equilibrium between the intracellular and extracellular protein pools and result also in decreased intracellular α-synuclein. Evidence suggests that α-synuclein in solution can penetrate lipid bilayers in cellular membranes and thereby become internalized or exported out of the cell. Finally, it can not be ruled out that α-synuclein also may exert toxic effects in the extracellular space.

The present invention is based on the use of stabilized soluble oligomers of α-synuclein. The molecular weight of human α-synuclein monomers is 14 kDa. Two or more α-synuclein monomers can aggregate and form soluble α-synuclein protofibrils/oligomers with a wide range of molecular weights. A dominating oligomer has a molecular weight around 2000 kD and is referred to as a protofibril. However, these soluble α-synuclein forms are instable and polymerize spontaneously to insoluble fibrils. The present invention stabilizes soluble oligomeric forms of α-synuclein and isolates the stabilized soluble oligomers, preferably in highly purified form, for antibody and vaccine development. The stabilized soluble α-synuclein oligomers according to the present invention exhibit a lower formation rate to a non-soluble aggregated form, i.e., fibrils, than a non-stabilized oligomer of the α-synuclein. These forms are of particular interest since they exhibit a high toxicity.

The invention uses various forms of α-synuclein as well as selected α-synuclein peptide fragments such as, but not limited to, derivatives of α-synuclein. In one embodiment, the α-synuclein oligomers are made from either synthetic or wild type human α-synuclein (SEQ ID NO: 1), or mutated form(s) thereof. As examples of mutated forms of human α-synuclein, any of the mutations A30P (SEQ ID NO: 2), E46K (SEQ ID NO: 3), A53T (SEQ ID NO: 4), or any combination thereof, including (A30P/E46K (SEQ ID NO: 5), A30P/A53T (SEQ ID NO: 6), E46K/A53T (SEQ ID NO: 7) or A30P/E46K/A53T (SEQ ID NO: 8)) can be used.

```
                                            SEQ ID NO: 1
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
                                            SEQ ID NO: 2
MDVFMKGLSK AKEGVVAAAE KTKQGVAEAP GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
                                            SEQ ID NO: 3
MDVFMKGLSK AKEGVVAAAE KTKQGVAEAA GKTKEGVLYV

GSKTKKGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
                                            SEQ ID NO: 4
MDVFMKGLSK AKEGVVAAAE KTKQGVAEAA GKTKEGVLYV

GSKTKEGVVH GVTTVAEKTK EQVTNVGGAV VTGVTAVAQK

TVEGAGSIAA ATGFVKKDQL GKNEEGAPQE GILEDMPVDP

DNEAYEMPSE EGYQDYEPEA
                                            SEQ ID NO: 5
MDVFMKGLSK AKEGVVAAAE KTKQGVAEAP GKTKEGVLYV

GSKTKKGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
                                            SEQ ID NO: 6
MDVFMKGLSK AKEGVVAAAE KTKQGVAEAP GKTKEGVLYV

GSKTKEGVVH GVTTVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

```
                                                    SEQ ID NO: 7
MDVFMKGLSK AKEGVVAAAE KTKQGVAEAA GKTKEGVLYV

GSKTKKGVVH GVTTVAEKTK EQVTNVGGAV VTGVTAVAQK

TVEGAGSIAA ATGFVKKDQL GKNEEGAPQE GILEDMPVDP

DNEAYEMPSE EGYQDYEPEA

SEQ ID NO: 8
MDVFMKGLSK AKEGVVAAAE KTKQGVAEAP GKTKEGVLYV

GSKTKKGVVH GVTTVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

In addition, other α-synuclein forms, with sequences deviating from the wild-type sequence, can be utilized. For example, wild type α-synuclein can be modified by replacing Ser/Ala with Cys, for example, via site-directed mutagenesis. One example of such is set forth by Chang, US 2006/0018918 A1, incorporated herein by reference.

Additionally, fragments, from the N-terminus, mid-portion and/or C-terminus of the α-synuclein protein, can be used to make the stabilized α-synuclein oligomers as well. In addition, fragments of wild-type or mutant α-synuclein, with a length of 1-10, 1-25, 1-35, 1-45, 1-79 or 1-95 amino acids can be used in any combination to make the oligomers. Such peptides can correspond to, but are not limited to the following number of amino acid sequence 1-95, 61-140, 95-140, 95-130, 95-120, 90-100, 100-110, 110-120, 120-130 and 130-140. Fragments can also be combined with full length α-synuclein. Fragments can also be branched or circulated before making the oligomers.

In addition to using recombinant protein or synthetic peptides, α-synuclein can be derived directly from Lewy bodies present in post mortem autopsied human brain tissue from cases with α-synucleinopathies. Both soluble (i.e. preparations soluble in Tris-buffered saline) and insoluble (i.e. preparations insoluble in Tris-buffered saline) α-synuclein fractions are purified. These sample preparations are either injected as such in mice, or fractionated by chromatographic methods before injection. The antibodies generated are used for treatment of patients in a passive vaccination scheme or in diagnostic immunoassays as described in further detail herein.

Alternatively, α-synuclein can be isolated by the combination of immunohistochemistry and laser-capturing microscopy by which Lewy bodies are visualized and targeted. For example, Lewy body-containing neurons are acquired from α-synuclein containing post mortem brain tissue by the combined use of laser capture microscopy and non-denaturing gel systems. For this application, α-synuclein species are extracted from polyacrylamide gel (see Example 3). More specifically, using chromatographic methods and non-denaturing gel systems, α-synuclein is purified from the captured tissue material and used as antigenic preparations that are injected into mice for the production of monoclonal antibodies. With this approach, a very diverse immunogenic response in the mice is obtained, generating antibodies with many different antigen affinities and specificities. Despite the diverse response when using the latter method, this approach may be advantageous when targeting an α-synuclein oligomer conformation that exists in the brain of Parkinson patients (Lewy bodies), which one would not be as likely to target with antibodies targeted against synthetic α-synuclein.

These mice can be used for obtaining α-synuclein oligomeric-specific monoclonal antibodies.

Furthermore, α-synuclein to be used for immunization of mice and monoclonal antibody development can also be isolated from biological tissues or fluids such as blood, cerebrospinal fluid, urine or saliva from healthy individuals or patients with α-synucleinopathies.

The stabilization of α-synuclein in soluble oligomeric form may be accomplished in various ways, such as for example structural modification. In one embodiment, the structural modification is achieved by binding to a stabilizing agent. The binding may be in the form of cross-linking. The stabilizing agent stabilizes the soluble oligomeric form such that further aggregation to non-soluble fibril conformation is prevented. In a specific embodiment, the soluble oligomer is a protofibril, and in a more specific embodiment, the protofibril has a molecular weight of about 2000 kD or more.

In a specific embodiment, the stabilizing agent is a hydrophobic organic agent. In various embodiments, the hydrophobic organic agent comprises a saturated, unsaturated, or polyunsaturated fatty acid, or derivative thereof, or any combination thereof, i.e., a combination of any two or more thereof. In further embodiments, the hydrophobic organic agent comprises a reactive aldehyde. The aldehyde may, for example, be an alkenal, such as an α,β-unsaturated aldehyde. Suitable reactive aldehydes include, but are not limited to, 4-hydroxy-2-nonenal, 4-oxo-2-nonenal (ONE), malondialdehyde and acrolein. The aldehyde may also be a dialdehyde having a mono or polyunsaturated carbon chain of 2-25 carbon atoms connecting the aldehyde groups. The hydrophobic organic agent stabilizes the soluble oligomer conformation, such that further aggregation to the non-soluble fibril conformation is prevented.

In a further embodiment, the α-synuclein can be modified by hydrophobic detergents such as, but not limited, non-ionic and zwitterionic detergents. Examples of such detergents included, but are not limited to, non-ionic detergents such as Triton X-100 (polyethylene glycol p-(1,1,3,3-tetramethylbutyl)-phenylether), Tween-20 (Polyoxyethylene (20) sorbitan monolaurate), Tween-80 (Polyoxyethylene (20) sorbitan monooleate), and Brij detergents (Polyoxyethylene ethers of fatty alcohols), and zwitterionic detergents such as CHAPS (3-[(3-cholamidopropyl)dimethylammonio]-1-propanesulfonate).

Other suitable stabilizing agents include bile acid derivatives, examples of which include but are not limited to, cholate, deoxycholate and taurocholate, and any combination thereof.

The stabilizing agent can also be selected from the group of natural biological molecules, examples of which include but are not limited to, triglycerides, phospholipids, sphingolipids, gangliosides, cholesterol, cholesterol-esters, long chain (for example containing about 6 to 30 carbon atoms) alcohols, and any combinations of the above agents.

Stabilization may also be accomplished using protein cross-linking agents such as, but not limited to, disuccinimidyl tartrate, bis-sulfosuccinimidyl suberimidate, 3,3-dithiobis-sulfosuccinimidyl propionate, and any combination thereof.

In another embodiment, the stabilized soluble α-synuclein oligomer comprises 1-alpha-hydroxy-secosterol as a stabilizing agent.

The stabilizing agents may be bound to, including by cross-linking, monomers and/or oligomers of α-synuclein, or combinations thereof, to form the stabilized soluble oligomers. For example, a reactive aldehyde such as HNE and/or ONE, may bind to the oligomers by way of the aldehyde group or a double bond, or both. The latter then results in cross-linkage of the oligomers. HNE, for example, may bind covalently to histidines and lysines of the oligomers. Similarly, ONE may bind covalently to histidines and lysines. The aldehydes may bind to lysine via a Shiff's base, or a histidine may bind via a nucleophilic attack on the carbon atom of a double bond in an unsaturated carbon chain. The stoichiometry between the stabilizing agent, for example, a reactive aldehyde, such as HNE and ONE, and α-synuclein can be varied within a wide range of 2:1 to 50:1 or higher. In a specific embodiment, HNE modification values above 20:1, e.g. 25:1, 30:1, 35:1, 40:1, 45:1, 50:1, and even higher, provide a product with desirably high protofibril formation. In addition, with ONE, an even lower ratio can be used, e.g. from 5:1, e.g. 10:1, 15:1, 20:1, 25:1, 30:1, 35:1, 40:1, 45:1, 50:1, and even higher.

If not stated otherwise, all of the stabilizing agents mentioned above impart their stabilizing effect by binding to α-synuclein and the stabilizing reaction may be conducted, for example, by incubation, as illustrated in the examples. The stabilizing agents may also be used in combinations of two or more as desired.

In yet another embodiment of the invention, the stabilized soluble α-synuclein oligomers may include one or more of β-amyloid (Aβ), tau or phospho-tau. These α-synuclein oligomers can be made by combining α-synuclein oligomers with β-amyloid (Aβ) oligomers, for example, protofibrils, made from Aβ40 and/or Aβ42. In yet another embodiment of the invention, these α-synuclein oligomers can be made by combining α-synuclein oligomers with β-amyloid protofibrils and tau and/or phospho-tau in any combination. In another embodiment, these α-synuclein oligomers are made by combining any combination of the individual monomers of α-synuclein, Aβ40, Aβ42, tau and/or phospho-tau, combining these proteins in their oligomer forms in any combination, or combining any oligomer with monomers. These mixtures are advantageous in that the additional components are found in patients with dementia, for example but not limited to, the Lewy body variant of Alzheimer's disease, and hence will provide therapeutically important neo-epitopes for antibody or vaccine treatment of these disorders (Tsigelny et al 2008). Another advantage is that the additional components will increase stability of α-synuclein protofibrils/oligomers.

In one embodiment, the invention is directed to a vaccine for delaying an onset of or for treatment of an α-synuclein-related disorder in an individual. In the present disclosure, the term vaccine is used to refer to a composition which is in a physiologically acceptable form for human or animal administration for active immunization. The vaccine comprises a therapeutically effective amount of isolated stabilized soluble α-synuclein oligomer having a lower formation rate to a non-soluble aggregated form than a non-stabilized oligomer of the α-synuclein. The term isolated refers to the stabilized soluble α-synuclein oligomer having been separated from preparation media, reactants and the like, including α-synuclein monomer and unreacted stabilizing agent. For a vaccine intended for administration to a human, the α-synuclein is human α-synuclein. For a vaccine intended for veterinary use, the α-synuclein is of the animal type of the intended recipient, i.e., canine α-synuclein for a vaccine for dogs. In specific embodiments, the vaccine comprises from about 10-500 microgram/dose of the stabilized soluble α-synuclein oligomer. In a more specific embodiment, the vaccine comprises from about 50-250 microgram/dose of the stabilized soluble α-synuclein oligomer.

The vaccine for active immunization may comprise one or more excipients as conventionally employed in the vaccine art, examples of which include, but are not limited to, one or more antibacterial agents, adjuvants, buffers, salts, pH-regulators, detergents, or a combination thereof, provided the excipients are pharmaceutically acceptable for human and/or veterinary use, depending on the intended vaccine recipient. The vaccine may also be freeze-dried, e.g. alone or together with one or more excipients to increase stability of the vaccine during and/or after freeze-drying. Specific examples of suitable excipients include, but are not limited to, mannitol and/or trehalose.

The invention is also directed to antibodies that bind soluble α-synuclein, including soluble α-synuclein monomer and soluble α-synuclein oligomers. The stabilized soluble α-synuclein oligomer may be used as an antigen to produce such antibodies and optimizes the development of specific antibodies against toxic forms of α-synuclein. In such methods, the antigen is administered to a non-human animal and the antibodies produced against said antigen are collected. In order to maximize the therapeutic effect, the antibodies raised against the stabilized α-synuclein antigen according to the present invention advantageously have a high reactivity against natural forms of soluble α-synuclein present in the body, in particular the aggregated soluble forms, including protofibrils, but also against the soluble α-synuclein monomer. One way of selecting such antibodies is to first screen for antibodies that bind modified and stabilized α-synuclein (in particular oligomers and specifically protfibrils) well and, subsequently, to screen among these antibodies for antibodies that bind well to wild type α-synuclein.

The resulting antibodies may be monoclonal or polyclonal antibodies, or active fragments thereof, that bind soluble α-synuclein, and particularly soluble α-synuclein before the α-synuclein can aggregate to fibrils. In specific embodiments, the stabilized soluble α-synuclein oligomer antigen may be used in methods such as hybridoma technology, phage display, ribosome display, mammalian cell display, and bacterial display, for producing and/or evolving monoclonal or polyclonal antibodies, or active fragments thereof. More specifically, for generation of monoclonal α-synuclein antibodies, a conventional technique, such as the hybridoma technique and/or phage display, ribosome display, mammalian cell display, or bacterial display may be employed. Such antibodies may be produced in rodents such as mouse, hamster or rat. Once generated, clones are isolated and screened for their respective antigen specificity. For screening, two principles are used. First, antibodies are probed against purified α-synuclein monomers, protofibrils/oligomers and fibrils. These different conformational forms of α-synuclein can be made by incubating stabilized soluble α-synuclein oligomer, for example, HNE-modified and/or ONE-modified α-synuclein, and subsequently fractionating by HPLC or using a centrifugal filter device. Fibrils can be isolated by centrifugation of the incubation mixture at above 5.000×g (see Example 1). Screening may be done by an enzyme-linked immunosorbent assay (ELISA) or by similar methods. Second, the antibodies are evaluated on tissue slices from α-synuclein transgenic animals and/or pathologic human brain tissue sections, containing Lewy bodies and Lewy neurites.

In additional embodiments, the antibodies react with both modified and stabilized, as well as unmodified α-synuclein, in mutated or wild type form of monomeric or aggregated soluble α-synuclein, or any combination thereof.

In one embodiment, the antibody according to the invention has higher binding strength to soluble α-synuclein oligomers, and, in a more specific embodiment, to α-synuclein protofibrils, particularly as compared with binding strength to α-synuclein monomers and insoluble fibrils. In a more specific embodiment, the binding strength ($IC_{50}$) for alpha-synuclein protofibrils compared to α-synuclein monomers is, for example, in the range of about 1:50-2000. In another specific embodiment, the binding strength ($IC_{50}$) for α-synuclein protofibrils compared to alpha-synuclein fibrils is, for example, in the range of about 1:2-2000.

The antibody may be human, humanized, or modified to reduce antigenicity in human patients. The reduction of antigenicity may for example be made by modifying or eliminating the T-cell epitopes of the antibody. In one embodiment, the antibody is selected from the IgG class, or more preferably from the IgG1 or IgG4 subclass (human antibody).

In additional embodiments, the antibody may also have reduced complement activity and/or altered Fc receptor binding properties. This may, for example, be achieved by mutating the Fc part of the antibody in positions 297, 322 or 331 of the amino acid sequence of the heavy chain (human), or the corresponding amino acids in, for example, mouse IgG. The reduced complement activity may also be achieved by deglycosylating the antibody enzymatically or by other means, in accordance with techniques known in the art. Altered Fc receptor binding properties of the antibody may be achieved by altering the oligosaccharide structures attached to the glycoprotein (Jeffries, *Nature*, 2009, 8: 226-234). The antibody may be a Fab fragment, for example selected from F(ab), $F(ab)_2$, and DiFabody, or a single chain antibody, for example selected from scFv-Fc and scFab, e.g. to improve blood brain barrier penetrance and neuronal cell uptake. It is therefore apparent that antibody as used herein refers to a full length protein raised by the antigen or an active fragment thereof.

In more specific embodiments, the α-synuclein oligomer antigen is fractionated and isolated by SEC-HPLC. The fractions are assessed for their respective toxicity in cell culture models and the antigen fractions with the strongest toxicity are selected as antigens for antibody production or as antigens for active immunization. The sample preparations can also be used directly to assess toxicity and the samples showing the most pronounced toxicity may advantageously be used as antigen for antibody selection and/or production or as antigens for active immunization.

The α-synuclein antibodies are formed as a response to administering the stabilized soluble α-synuclein according to the present invention, either directly to the patient (active immunization) or by immunizing a rodent, for example a mouse or a rabbit, in order to raise monoclonal or polyclonal antibodies against the antigen, which are applied in a passive immunization protocol to treat neurodegenerative disorders with α-synuclein pathology, e.g. PD and DLB, just to mention a few. In the case of passive immunization, the antibodies are humanized before being administered to a human patient.

Figure 2A:
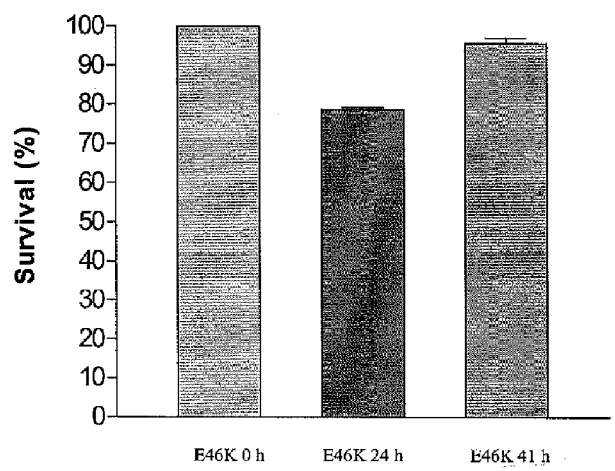
FIG. 2A shows a decreased survival among human embryonic kidney (HEK-293) cells that have been treated with α-synuclein E46K preparations incubated for 24 and 41 hours. The α-synuclein E46K preparation incubated for approximately 24 hours showed the highest toxicity. When non-incubated (time zero) α-synuclein is added to HEK293 cells, no toxic effect was observed.
Figure 2B:
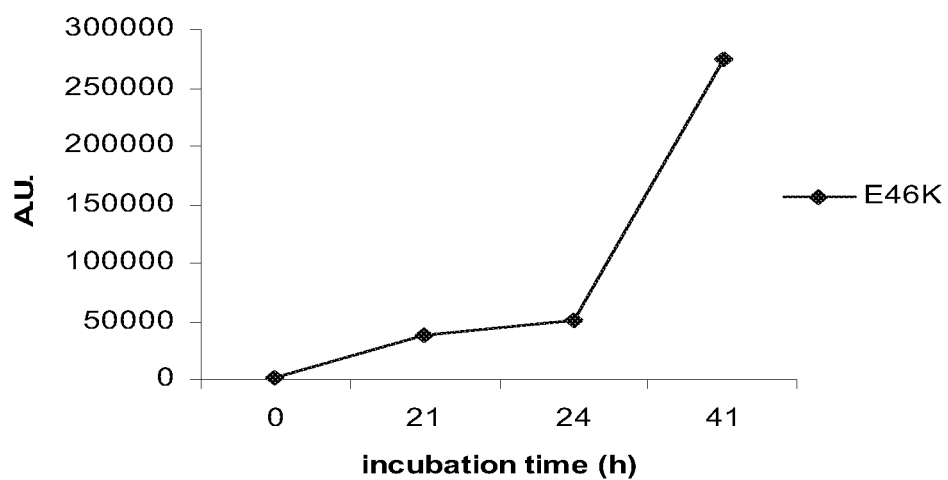
FIG. 2B shows the α-synuclein E46K preparation exhibited moderate ThT signals after 24 hours incubation, i.e., the degree of fibrillization is moderate. In contrast, samples incubated for 41 hours containing fibrillar forms of α-synuclein and exhibiting a high ThT signal, showed almost no toxic effect.
Figure 3:
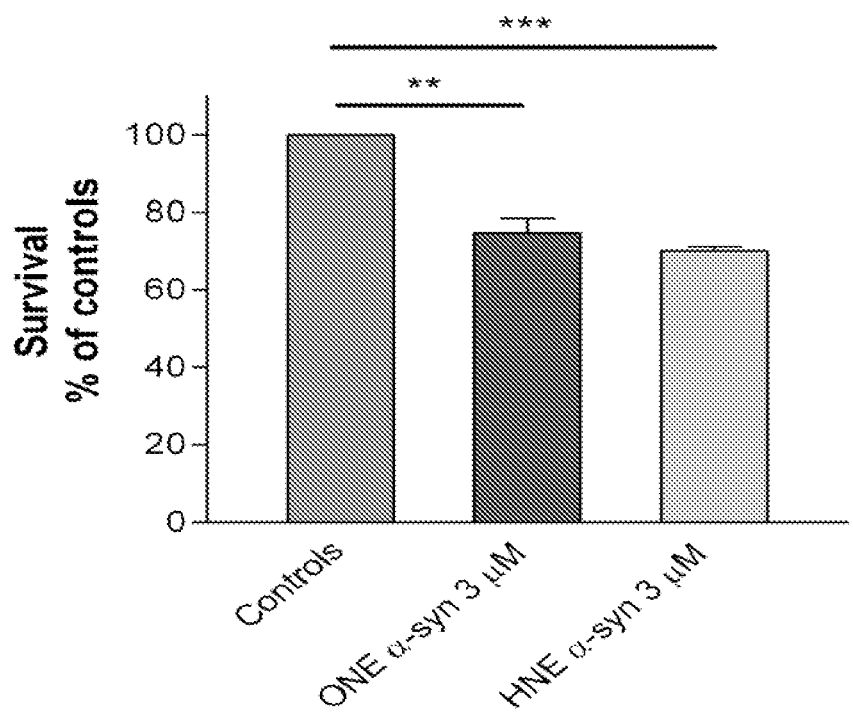
FIG. 3 shows a decreased survival among human embryonic kidney (HEK-293) cells that have been treated with ONE- and HNE-stabilized wt α-synuclein protofibrils/oligomers which were added exogenously to the cells and incubated for 48 h. As percent of controls, a significant decrease in cell survival was detected for cells treated with 3 μM ONE-modified α-synuclein (p<0,001) and cells treated with 3 μM HNE-modified α-synuclein (p<0.0001). Data are expressed as percentage of vehicle control and represent the mean value±SEM for three separate experiments.

The toxicity of the aggregated forms of α-synuclein may be determined by various cell toxicity assays (see FIGS. 2-3 and Example 5). In brief, one cell culture model is based on assessment of MTT, a measure of mitochondrial dysfunction. Other toxicity assays, for example, measuring cell death or apoptotic markers, may also be used. Examples thereof include, but are not limited to, adenylate kinase analysis, lactate dehydrogenase analysis, annexin-V staining, caspase activity, PARP cleavage and DNA laddering.

Following an active immunization protocol, the selected stabilized α-synuclein antigen is administered to yield conformation-specific antibodies directed towards α-synuclein species with pronounced toxicity, in particular soluble protofibrillar and other oligomeric α-synuclein and α-synuclein monomer. Following a passive immunization protocol, monoclonal or polyclonal antibodies against such α-synuclein species exert their effect upon repeated injections of the antibodies.

In an alternate embodiment, the antibody which binds soluble α-synuclein may be human anti-α-synuclein monoclonal antibodies derived from white blood cells from control human subjects or patients with α-synucleinopathies. Hybridomas are made from the white blood cells according to established techniques and screened for binders to α-synuclein and stabilized α-synuclein (for example soluble oligomers). Human anti-α-synuclein monoclonal antibodies can also be obtained by screening a human antibody library for binding to stabilized α-synuclein (for example soluble oligomers). Autoantibodies against soluble α-synuclein or α-synuclein protofibrils/oligomers present in blood from human control subjects or patients with α-synucleinopathies may also be isolated for use. These autoantibodies can be sequenced and made by recombinant-DNA technology in for example CHO cells to improve yield and economy.

In a specific embodiment, the antibody as described is provided in a composition, for example, suitable for administration. Such compositions may comprise an antibody as described herein and one or more excipients conventionally employed in pharmaceutical compositions. The antibody will be included in a therapeutically effective amount. In a specific embodiment, the compositions comprise the antibody in an amount of about 0.1-5 mg/kg, or more specifically, about 0.5-2 mg/kg, of body weight of the intended recipient.

Suitable excipients include, but are not limited to, one or more antibacterial agents, adjuvants, buffers, salts, pH-regulators, detergents, or any combination thereof, provided that such excipients are pharmaceutically acceptable for human and/or veterinary use, depending on the intended recipient. The composition may be freeze-dried, for example, alone or together with an excipient to increase stability of the antibody during and/or after freeze-drying. Mannitol and/or trehalose are non-limiting examples of excipients suitable for the freeze-drying.

The vaccines and antibodies as described herein may be used in one or more methods for preventing, delaying an onset of, or treating an α-synuclein-related disorder in an individual. Such methods comprise administering an antibody or vaccine as described herein to the individual. The individual is, for example, a subject suspected of having acquired or having an increased risk of acquiring an α-synuclein-related disorder. A subject could be suspected of having such a disorder by displaying any of the following characteristics: early disease symptoms, positive brain imaging results, and/or increased levels of α-synuclein or α-synuclein oligomers (e.g. as determined by utilizing antibodies as described herein, for example in a detection method as described herein). Examples of brain imaging methods include, but are not limited to DaTscan ($^{123}$I-Ioflupane), or Positron Emission Tomography (PET) imaging by using a monoclonal antibody as described herein.

By identifying subjects at risk of or suspected of having an α-synuclein-related disorder, further development of the disorder is prevented or onset or progression is delayed by the inventive treatments described herein, i.e. by using active or passive immunization with the vaccines/antigens or antibodies. The α-synuclein-related disorder may be Parkinson's disease (PD), dementia with Lewy bodies (DLB), the Lewy body variant of Alzheimer's disease, multiple system atrophy (MSA) or other neurodegenerative disorder with α-synuclein pathology, including other neurodegenerative disorders such as Alzheimer's disease, Down's syndrome, amyotrophic lateral sclerosis, frontotemporal dementia, Huntington's disease, prion disease, Creutzfeldt Jakob's disease, Gerstmann-Sträussler-Scheinker syndrome, Kuru, fatal familial insomnia, cerebrovascular amyloidosis, Glaucoma, age-related macular degeneration, psychiatric syndromes, schizophrenia and/or schizophrenia-like disorders.

The antibodies of the invention as described herein may also be used in detection methods, a specific example of which includes diagnostic immunoassays in which the antibodies are used to detect altered levels of the α-synuclein species in vitro and in vivo. Levels of the targeted forms of α-synuclein may be specifically changed in different tissues and body fluids from patients with different α-synucleinopathies or other neurodegenerative disorders and thus serve as early biochemical markers for Parkinson's disease (PD), dementia with Lewy bodies (DLB), the Lewy body variant of Alzheimer's disease, multiple system atrophy (MSA) or other neurodegenerative disorders with α-synuclein pathology.

More specifically, a method of detecting α-synuclein oligomers in vitro comprises adding the antibody according to the invention to a biological sample comprising or suspected of comprising soluble α-synuclein, and detecting and measuring a concentration of any complex formed between the antibody and soluble α-synuclein. The biological sample may be, for example, plasma, cerebrospinal fluid (CSF) or a brain biopsy. In another embodiment, a method of detecting α-synuclein oligomers in vivo comprises administering an antibody according to the present invention, said antibody being labelled with a detectable marker, to an individual suspected of carrying unhealthy soluble α-synuclein oligomeric levels or species in the brain, and detecting the presence of any complex formed between the antibody and soluble α-synuclein by detection of the marker.

For labeling of the oligomer-specific antibody, one of ordinary skill in the art will recognize that various alternative techniques may be used, depending on the choice of detection method, e.g. radioactive ligands such as $^{131}$I, $^{14}$C, $^{3}$H or $^{58}$Ga, just to mention a few. In particular, PET with a radiolabelled oligomer-specific antibody is believed to be of great importance for diagnosis, therapy monitoring, and/or the like. Accordingly, the invention provides antibodies that are easily labeled by one of ordinary skill in the art using conventional techniques, for use in various methods for diagnosis and therapy monitoring.

In accordance with the methods and techniques described, the antigens and antibodies described herein may be evaluated for their therapeutic potential in cell culture modes and/or transgenic animal models for α-synuclein pathology. Examples of two cell culture models for α-synucleinopathy can be used. Firstly, wild type or mutant forms of α-synuclein DNA are transfected to neuroblastoma or neuroglioma cells. Both transient and stable transfections are performed on cells that are differentiated to a neuron-like morphology by retinoic acid. In this way, it is possible to induce the formation of intracellular α-synuclein aggregates. Secondly, α-synuclein DNA vector-carrying lenti- and/or adeno-associated virus (AAV) are transduced on cultures of neuroblastoma, neuroglioma and/or embryonic kidney cell cultures. Transduction with viral vectors is advantageous to traditional transfection techniques as it is generally more efficient, allowing more cells to form α-synuclein aggregates.

The generated α-synuclein antibodies are also utilized in immunobased assays for the measurement of α-synuclein (in particular protofibril/oligomer) levels in patient samples to diagnose PD, DLB or other α-synucleinopathies. The detection methods applied in the diagnostic assay are mainly based on immunoassays, such as enzyme-linked immunosorbent assay (ELISA) and/or Western blot. A broad range of tissues from patients with early signs of α-synucleinopathy or individuals with a high risk of developing these disorders are investigated for their levels of α-synuclein protofibrils/oligomers, or other forms of conformationally altered soluble α-synuclein. Such tissues include, but are not limited to, plasma, cerebrospinal fluid (CSF) and brain biopsies.

Various aspects of the invention are illustrated in the following Examples.

EXAMPLES

Example 1

Aggregation Kinetics of Wild-Type and Mutated Forms of α-Synuclein

The effect of the different α-synuclein mutations are investigated in vitro. In addition to wild type α-synuclein, the following mutants are studied: A30P, E46K, A53T and A30P/A53T, A30P/E46K, E46K/A53T and A30P/E46K/A53T. Recombinant α-synuclein is expressed by using the IMPACT (Intein Mediated Purification with an Affinity Chitin-binding Tag, New England Biolabs, Ipswich, Mass., USA) system, according to the manufacturer's instructions. All recombinant proteins are dissolved in Tris-buffer, or phosphate buffer, ranging in concentration between 10 mM and 50 mM with or without NaCl ranging in concentration between 0.05M and 0.3M. All recombinant α-synuclein proteins are stored at −80° C. before use.

For additional studies, recombinant proteins are dissolved in sodium acetate or citrate buffer within the pH range of 3-6, with or without NaCl in the concentration between 0.05M and 0.3M. Initial protein concentrations vary from 35 µM to 750 µM and are similar for all types of α-synuclein species in each experiment. In some experiments, thioflavin T (5-20 µM) is added to the initial reaction mixture with a final α-synuclein concentration of 10 µM.

When studying aggregation kinetics, α-synuclein preparations are kept in a flat or round bottom polypropylene 96 well plate (Greiner Bio-One, Frickenhausen, Germany), or a flat bottom non-binding polystyrene 96 well plate (Greiner Bio-One, Frickenhausen, Germany) and incubated between 4° C. and 65° C. with or without agitation. In the same experiments, polypropylene microtubes (500-2000 µl), uncoated or coated with silicon, are incubated between 4° C. and 65° C. with or without agitation. For studies when agitation is used, either a polypropylene 96 well plate, or a horizontally placed microtube (500-2000 µl), are incubated on a Labnet P4 orbital shaker (Labnet, Edison, N.J., USA) or a Titramax 101 (Heidolph Instruments GMBH & Co.KG, Schwabach, Germany) with the speed varying between 300 rpm and 900 rpm. In all aggregation studies a final volume of 100-300 µl per well is used. In aggregation experiments in which a microtube is used, the final volume ranges from 100-2000 µl. For ThT measurements, the polystyrene or polypropylene 96 well plates are read in a Wallac Victor 2 (PerkinElmer, Waltham, Mass., USA), equipped with a 445 nm excitation filter and a 485 nm emission filter. The results from α-synuclein featuring some of these mutations are shown in FIG. 1.

Example 2

Synthesis of α-Synuclein Protofibrils/Oligomers

To produce α-synuclein protofibrillar/oligomeric antigen (i.e., antigen containing protofibrils and other oligomers), the respective wild type, mutated or fragmented α-synuclein, as described above, is used in a concentration of 35-750 µM. In samples in which α-synuclein has been conjugated to HNE and/or ONE (Cayman Chemical, Ann Arbor, Mich., USA), these compounds are used at a concentration of 0.01-65 mM. In a typical experiment, the molar ratio between HNE and/or ONE and α-synuclein ranges between 1:1 and 100:1, but the proportion of the respective compounds is not limited to this stoichiometry. In certain experiments sodium borohydride (NaBH$_4$) is used at concentration of 0, 1-100 mM to reduce the HNE-modified and/or ONE-modified samples. In some cases, the α-synuclein amino acid may contain amino acids (such as lysine) that during the HNE-modification forms an unstable and reversible Skiff's base that binds with HNE. In another case, the α-synuclein amino acid may contain amino acids (such as lysine) that during the ONE-modification forms an unstable and reversible Shiff's base that binds with ONE. The sodium borohydride reduction stabilizes the Skiff's base binding. The samples are incubated at 37° C. with or without agitation for 30 minutes to 30 days. To verify the molecular composition of the samples, several methods are utilized. Unmodified α-synuclein or HNE-modified and/or ONE-modified α-synuclein or α-synuclein modified with other reactive aldehydes, are centrifuged at 16. 900×g for five min. at 21° C. to remove any insoluble fibrils. The supernatant is subsequently fractionated using a SEC-HPLC system with UV detection between 214 nm and 280 nm (described in detail below) to isolate α-synuclein protofibril oligomers and monomers. In another experiment, α-synuclein protofibrils/oligomers and monomers are separated using a centrifugal filter device with a molecular cutoff between 5-1000 kDa. In a typical experiment, samples, 500 µl HNE and/or ONE-modified α-synuclein, are centrifuged using either a Microcon centrifugal filter device (Millipore, Billerica, Mass.) or a Vivaspin 500 centrifugal device (Sartorius, Goettingen, Germany) with a cutoff value of 100 kDa. The samples are centrifuged at a speed varying between 1000-15000×g for 5-30 min and the retenate is collected and contains the majority of the α-synuclein protofibrils/oligomers.

HNE-Modified α-Synuclein

Figure 4:
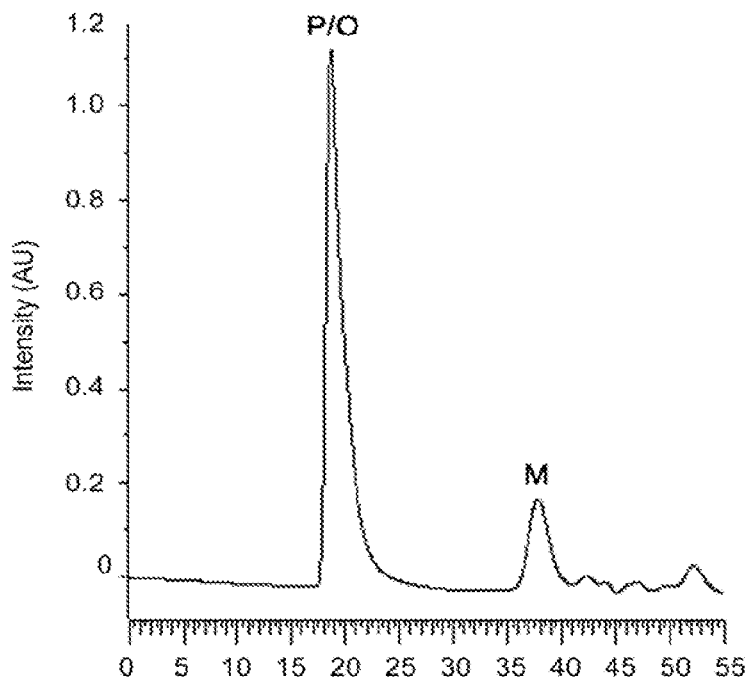
FIG. 4 shows a SEC-HPLC chromatogram of a HNE-modified α-synuclein preparation incubated at 37° C. for 20 hours using a stoichiometry between HNE and α-synuclein of 30:1. The main peak, eluting at 19 min (P/O), corresponds to α-synuclein soluble protofibrils/oligomers. The second peak, eluting at 37 min (M), corresponds to monomeric α-synuclein.

In a typical experiment 140 µM human wild-type α-synuclein is incubated with 5.6 mM HNE (i.e. with a ratio of 40:1 between HNE and α-synuclein) for 20 hours at 37° C. after which the excess of unbound HNE is removed using either Zeba desalt spin columns (Pierce Biotechnology, Rockford, Ill., USA), Vivaspin 500 centrifugal device (Sartorius, Goettingen, Germany) or a Microcon centrifugal filter device (Millipore, Billerica, Mass.) according to the manufacturer's instructions. After this initial HNE-modification step, samples are analyzed directly. Prior to SEC-HPLC analysis, all samples are subjected to centrifugation at 16.900×g for 5 min. at 22° C. and only the soluble fraction is analyzed by SEC-HPLC using a Superose 6 PC3.2/30 column. The α-synuclein protofibrils/oligomers elute in a peak at 19 min. whereas the α-synuclein monomers elute at 37 min. (FIG. 4).

ONE-Modified α-Synuclein

Figure 5:
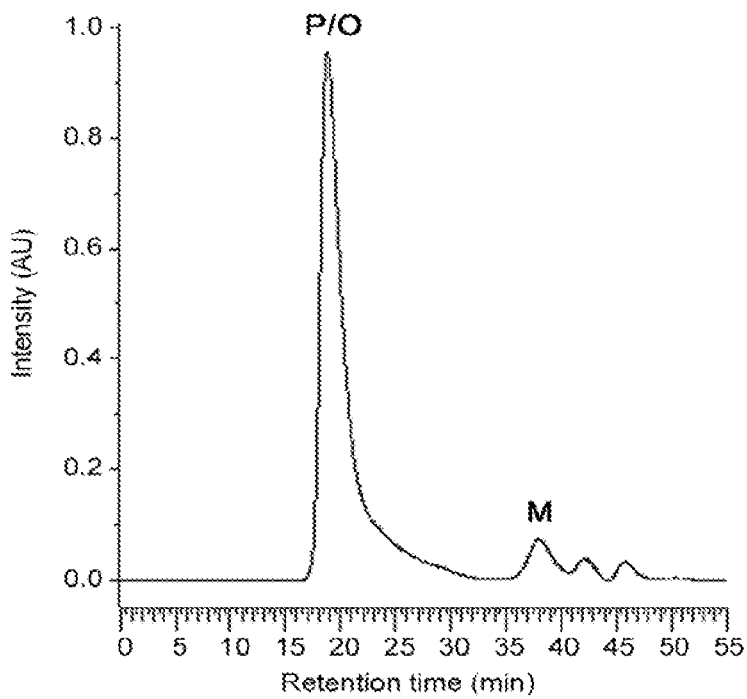
FIG. 5 shows a SEC-HPLC chromatogram of ONE-modified wild-type α-synuclein incubated at 37° C. for 20 hours using a stoichiometry between ONE and α-synuclein of 30:1. One main peak (P/O) is observed at 19 min and corresponds to soluble α-synuclein protofibrils/oligomers. An additional peak is observed, eluting at 37 min (M) and which corresponds to α-synuclein monomers.

In a typical experiment human wild-type α-synuclein (140 µM) is incubated with 4.2 mM ONE (i.e. with a ratio of 40:1 between ONE and α-synuclein) for 20 hours at 37° C. and the excess of unbound ONE is removed using Zeba desalt spin columns (Pierce Biotechnology, Rockford, Ill., USA), Vivaspin 500 centrifugal device (Sartorius, Goettingen, Germany) or a Microcon centrifugal filter device (Millipore, Billerica, Mass.) according to the manufacturer's instructions. Prior to SEC-HPLC analysis, all samples are subjected to centrifugation at 16.900×g for 5 min. at 22° C. and only the soluble fraction is analyzed by SEC-HPLC using a Superose 6 PC3.2/30 column. The α-synuclein protofibrils/oligomers elute as the main peak at 20 min. whereas a small amount of α-synuclein monomers elute at 37 min. (FIG. 5).

HNE- and ONE-Modified α-Synuclein

In a typical experiment human wild-type α-synuclein (140 µM) is incubated with 4.2 mM HNE and 4.2 mM ONE for 20 hours at 37° C. and the excess of unbound HNE and ONE is removed using Zeba desalt spin columns (Pierce Biotechnology, Rockford, Ill., USA), Vivaspin 500 centrifugal device (Sartorius, Goettingen, Germany) or a Microcon centrifugal filter device (Millipore, Billerica, Mass.) according to the manufacturer's instructions. All samples are subjected to centrifugation at 16.900×g for 5 min. at 22° C. and only the soluble fraction is analyzed by SEC-HPLC using a Superose 6 PC3.2/30 column.

Example 3

HPLC Separation of α-Synuclein Species

To isolate α-synuclein protofibrils/oligomers, monomers and fibrils, α-synuclein is incubated as described above. A Merck Hitachi D-7000 LaChrom HPLC system, having a diode array detector model L-7455, a L-7200 model autosampler and a model L-7100 pump, coupled to a Superdex 75 PC3.2/30, Superdex 200 PC3.2/30 or a Superose 6 PC3.2/30 column (GE Healthcare, Uppsala, Sweden), is used for chromatographic separation and purity analysis. Samples are eluted at flow rates varying between 0.02 ml/min and 0.08 ml/min using either 20-50 mM Tris pH 6.0-8.0, 0.15M NaCl or 20-50 mM sodium phosphate pH 6.0-8.0, 0.15 M NaCl. Alternatively, a Hitachi LaChrome Elite HPLC system, having a model L-2130 pump, a diode array detector model L-7450, a L-2200 autosampler, coupled to a Superose 6 10/300 GL, a Superdex 200 100/300 GL or a Superdex 75 100/300 GL is used. Samples are eluted at flow rates varying between 0.1 ml/min and 0.5 ml/min using either 20-50 mM Tris pH 6.0-8.0, 0.15M NaCl or 20-50 mM sodium phosphate pH 6.0-8.0, 0.15 M NaCl. Moreover, samples can be eluted with a sodium acetate buffer or sodium citrate buffer with a pH between 3 and 6 with 0.15M NaCl. In some SEC-HPLC analyses, 0.1%-2.0% Tween-20 or Tween-80 is added to the elution buffer to reduce non-specific adherence of α-synuclein protofibril oligomers to the column matrix. Chromatograms are obtained by measuring UV absorbance between 214 nm and 280 nm. Fractions of 20-100 µl are collected on an Advantec SF-3120 (Advantec, Kashiwa, Japan), fraction collector. Fractions of 50-500 µL1 can also be collected on a Bio-Rad model 2128 (Bio-Rad, Hercules, Calif.) fraction collector. Globular molecular weight standards are used to obtain a standard curve, from which retention times of the various α-synuclein species are correlated to molecular weight.

Example 4

Characterization of α-Synuclein Protofibrils/Oligomers

Figure 6:
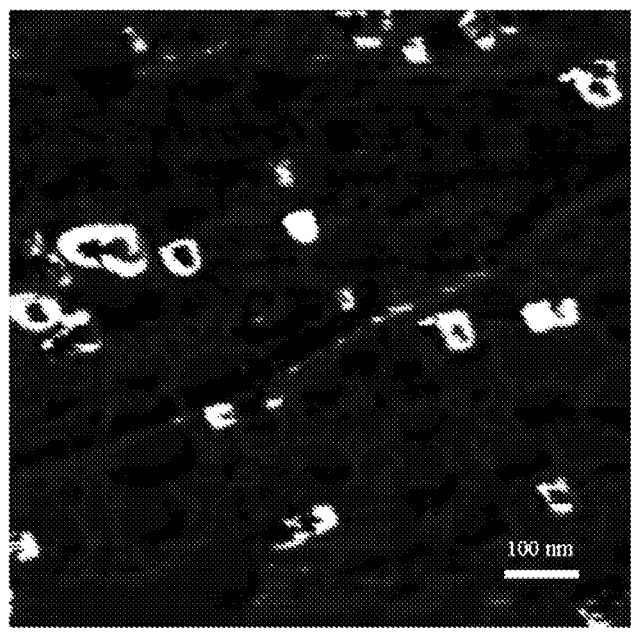
FIG. 6 shows an atomic force microscopy (AFM) image of isolated soluble α-synuclein protofibril/oligomer modified with HNE. For example, protofibrils/oligomers exhibiting a ring-like structure that has a hollow core and a diameter of about 50-300 nm are observed. Scale bar represents 100 nm.
Figure 7:
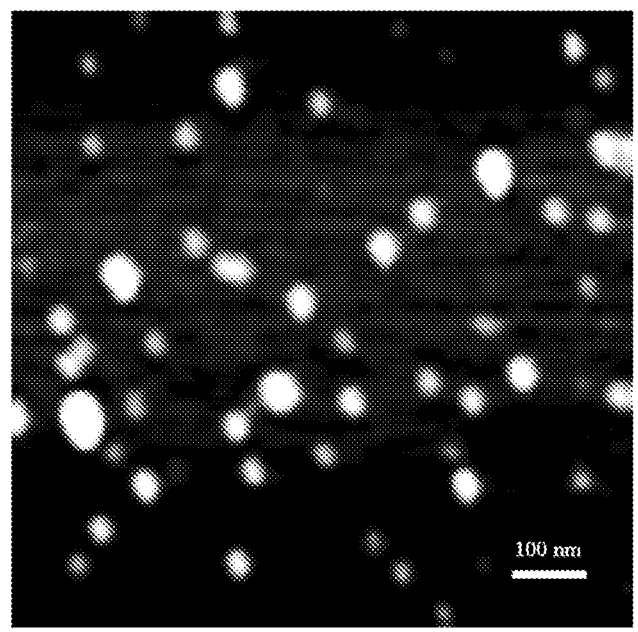
FIG. 7 shows an AFM analysis of isolated soluble α-synuclein protofibrils/oligomers modified with ONE. In a typical sample, protofibrils/oligomers with an amorphous appearance and a diameter of about 30-150 nm are observed. Scale bar represents 100 nm.

To further characterize the morphology of the isolated α-synuclein protofibrils/oligomers, cryoelectron microscopy and atomic force microscopy (AFM) are performed. Protein aliquots of 1-100 µl are diluted to a final concentration varying between 10 µM and 350 µM, added to a mica surface or a HOPG surface (Veeco instruments SAS, Dourdan cedex, France) and analyzed according to standard protocols. The AFM analysis of the HNE-modified α-synuclein protofibrils/oligomers reveal a heterogeneous population of both ring-like and more linear and round structures varying in diameter between 50-300 nm. For example, annular molecular species with a ring-like structure with a diameter between 50-300 nm can be observed (FIG. 6). AFM analysis of ONE-modified α-synuclein reveals amorphous structures with a diameter of about 30-150 nm in width (FIG. 7).

Example 5

α-Synuclein Toxicity Evaluation

The effect of in vitro-aggregated unmodified α-synuclein and HNE and/or ONE-modified α-synuclein oligomer is analyzed on a cell culture model utilizing the commonly used MTT (Sigma-Aldrich, St. Louis, Mo., USA)-viability assay. The cell types used in the study include HEK-293, SH-SY5Y cells and H4 cells. Other assays measuring cell death and apoptotic markers used in the study include ToxiLight (Lonza, Basel, Switzerland) and the Lactate dehydrogenase assay (Cayman Chemical, Ann Arbor, Mich., USA). Wild type α-synuclein is compared to the following mutants: A30P, E46K, A53T, A30P/E46K, A30P/A53T, A30P/E46K and A30P/E46K/A53T. Cells are grown in DMEM (Invitrogen, La Jolla, Calif., USA) supplemented with 10% of fetal calf serum (Cambrex, Charles City, Iowa, USA). In one type of experiment, cells are kept in an incubator at 37° C. and 5% $CO_2$. The day before starting the toxicity assay, HEK-293 cells are seeded in 96-well polystyrene coated plates (Sarstedt, N.C., USA) with a density of 10000 cells/well. Next, cell media is removed and cells are treated with aggregated forms of unmodified α-synuclein diluted in fresh conditioned media at a final concentration ranging from 3 µM to 6 µM. In another set of experiments ONE- and/or HNE-modified α-synuclein oligomer is diluted in fresh conditioned media at a final concentration ranging from 3 µM to 6 µM. After 48 hours of incubation, MTT, diluted in phosphate-buffered saline (Invitrogen, La Jolla, Calif., USA), is added to cells at a final concentration of 35 µM. After 4.5 hours of incubation, cells are treated with a mixture of 50% DMF and 20% SDS (Sigma-Aldrich, St Louis, Mo., USA) and this mixture is incubated for an additional 24 hours. Finally, for measurement of the metabolized substrate, a Spectra Max 190 spectrophotometer (Molecular Devices Corporation, CA, USA) is used and detection is carried out at 570 nm.

Example 6

α-Synuclein Antibodies in Mice Immunized with α-Synuclein Protofibrils/Oligomers Immunization/Polyclonal Antibodies In the immunization scheme Balb/C mice are utilized. For the first immunization, mice are injected with 50 µl Freunds complete adjuvant and 50 µl HNE-modified and/or ONE-modified α-synuclein protofibrillar/oligomer preparations (final concentration 35 µM). For the initial immunizations (e.g. 3-6 times) mice are injected with 50 µl Freunds incomplete adjuvant and 50 µl HNE-modified and/or ONE-modified α-synuclein protofibrillar/oligomer preparations (final concentration 35 µM). For subsequent immunizations (e.g. 1-3 times), mice are injected with 50 µl HNE-modified and/or ONE-modified α-synuclein protofibrillar/oligomer preparations (final concentration 35 µM) diluted in Tris-buffered saline or phosphate-buffered saline, pH 7.4. Two booster injections, containing 50 µL1 HNE-modified and/or ONE-modified α-synuclein protofibrillar/oligomeric preparations (final concentration 70 µM), are carried out prior to the mice being sacrificed.

Blood from immunized mice are analyzed for reactivity toward HNE-modified (FIG. 8) and ONE-modified (FIG. 9) α-synuclein protofibrils/oligomers. The specificity of the polyclonal antibody response is analyzed by ELISA. In a typical experiment, a flat bottom high binding 96-well polystyrene microtiter plate is coated with monomeric α-synuclein (unmodified or modified with HNE and/or ONE, or other aldehydes), protofibrillar/oligomeric α-synuclein (unmodified or modified with HNE and/or ONE, or other aldehydes) or fibrillar α-synuclein at a final concentration of 400 ng/well. The wells are blocked with 2% BSA, washed with 0.05% Tween-20/PBS and cell media supernatants (undiluted or diluted 1:1 with phosphate-buffered saline) from investigated polyclonal antibodies are added to the wells as primary antibodies. Alkaline phosphatase-conjugated goat anti-mouse IgG/IgM antibody (Pierce Biotechnology, Rockford, Ill., USA) is used as the secondary antibody at a dilution of 1/1000 Immunoreactivity is visualized using p-nitrophenylphosphate (Sigma-Aldrich, Mo., USA).

Figure 8:
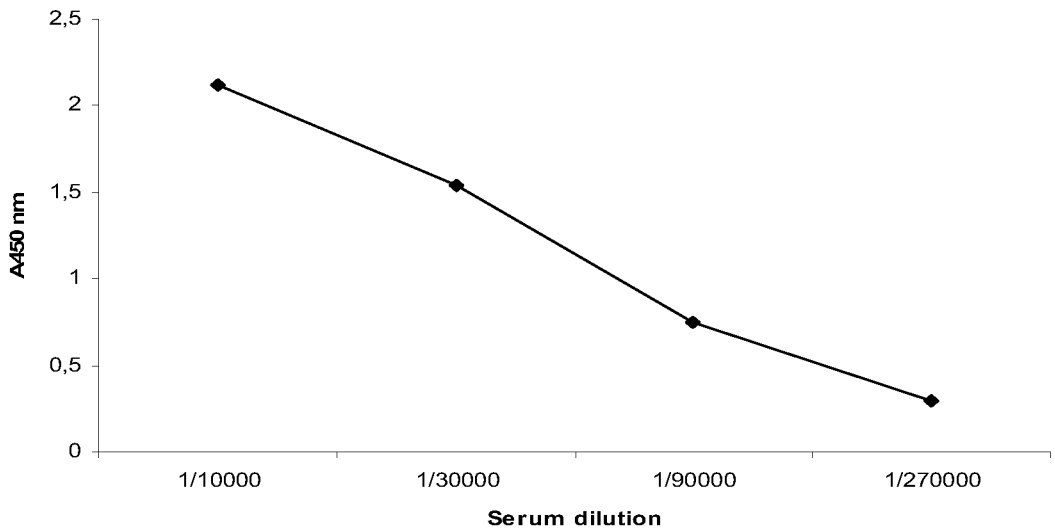
FIG. 8 shows an ELISA on serum (1/10000-1/270000 dilution) from a mouse immunized with a soluble protofibril/oligomer preparation of HNE-modified wild-type human α-synuclein. Antibodies that recognize HNE-modified α-synuclein protofibrils/oligomers are detected in the serum.
Figure 9:
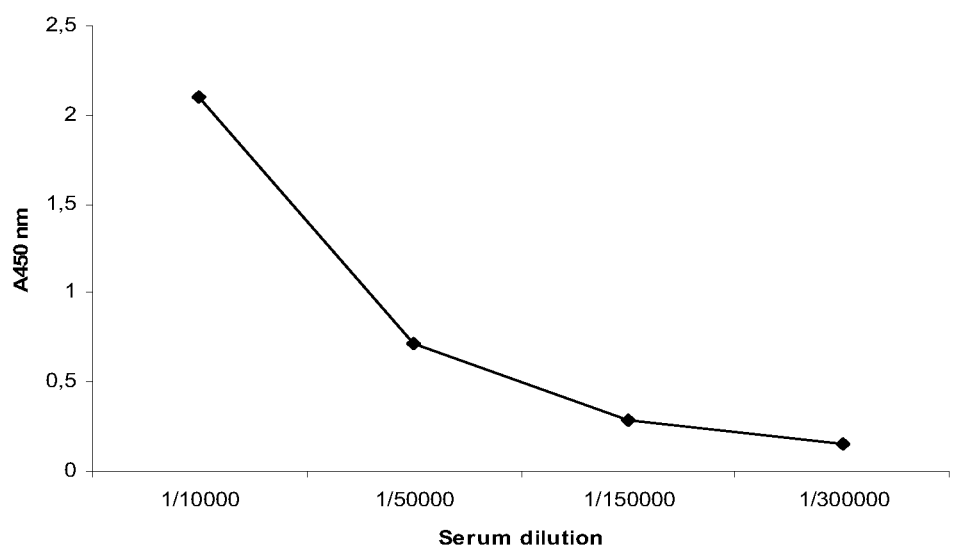
FIG. 9 shows an indirect ELISA on serum (1/10000-1/300000 dilution) from a mouse immunized with soluble ONE-modified wild-type α-synuclein protofibrils/oligomers. Antibodies that recognize α-synuclein protofibrils/oligomers are detected in the serum.

In the serum, antibodies that specifically recognize α-synuclein protofibrils/oligomers are detected (FIGS. 8 and 9).

Hybridoma/Monoclonal Antibodies

Spleen cells are isolated and grinded in sterile phosphate-buffered saline (PBS) and centrifuged at 1200×g for 10 min to collect a cell-rich pellet. The cells are further washed with PBS and centrifuged at 1200×g for 10 min. The cell pellet is resuspended in Dulbecco's minimum essential medium (DMEM, Invitrogen, La Jolla, Calif., USA) supplemented with 1% antibiotics. Spleen cells are mixed at a 1:1 ratio with Sp2/0 cells (mouse myeloma cell line) in DMEM. To facilitate cell fusion, 1 ml of polyethylene glycol (Sigma-Aldrich, St. Louis, Mo., USA) is added to the cell mixture and the reaction is stopped with the addition of DMEM. Cells are harvested and the pellet is resuspended in DMEM supplemented with 10% (v/v) fetal bovine serum (Cambrex, Charles City, Iowa, USA) and also containing 1% (v/v) sodium pyruvate (Cambrex, Charles City, Iowa, USA), 1% (v/v) antibiotics (Sigma-Aldrich, St. Louis, Mo., USA) and 1% (v/v) L-glutamine (Cambrex, Charles City, Iowa, USA). After centrifugation, the final cell pellet is resuspended. To investigate the antibodies produced by the generated hybridomas, an ELISA protocol is used. In a typical experiment, a flat bottom high binding 96 well polystyrene microtiter plate is coated with monomeric α-synuclein (unmodified or modified with HNE and/or ONE, or other aldehydes), oligomeric/protofibrillar α-synuclein (unmodified or modified with HNE and/or ONE, or other aldehydes) or fibrillar α-synuclein at a final concentration of 400 ng/well. The wells are blocked with 2% BSA, washed with 0.05% Tween-20/PBS and cell media supernatants (undiluted or diluted 1:1 with phosphate-buffered saline) from investigated hybridoma are added to the wells as primary antibodies. Horseradish peroxidise-conjugated goat anti-mouse mouse IgG/IgM antibody (Pierce Biotechnology, Rockford, Ill., USA) is used as the secondary antibody at a dilution of 1/5000 Immunoreactivity is visualized using an enhanced K-Blue® substrate (TMB) and the reaction is stopped with 2M $H_2SO_4$. DMEM supplemented with 10% fetal bovine serum and also containing 5% (v/v) BM condition media (Roche Diagnostics Scandinavia, Bromma, Sweden) and 2% (v/v) HAT media supplement (Sigma-Aldrich, St. Louis, Mo., USA) and cells are plated on 96 well cell culturing plates.

Figure 10:
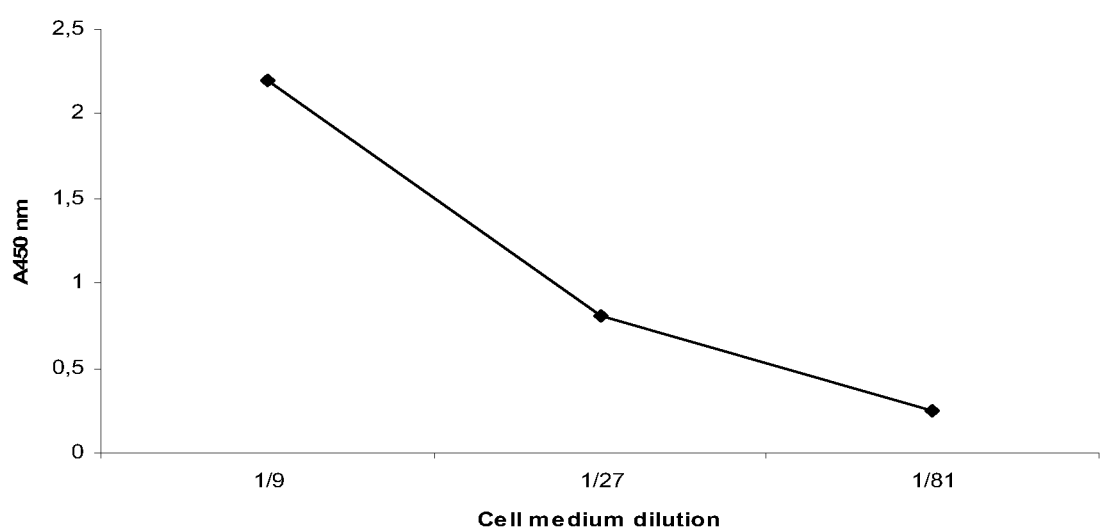
FIG. 10 shows an ELISA of a α-synuclein protofibril reactive monoclonal antibody. A positive signal was obtained with all three dilutions (1/9, 1/27 and 1/82) of the cell medium from hybridoma 40:2 when ONE-modified wild-type α-synuclein protofibrils/oligomers were used as antigen. Background signal has been deducted from all OD values.

Hybridomas were generated by injecting ONE-modified α-synuclein protofibrillar/oligomer preparations as previously described. Specifically, the hybridoma 40:2 recognized a ONE-modified α-synuclein protofibrillar/oligomer preparation in an ELISA protocol. Cell media supernatant from the hybridoma 40:2 was diluted to 1/9, 1/27 and 1/82 and was analyzed as described above on a flat bottom high binding 96 well polystyrene microtiter plate coated with 400 ng/well of ONE-modified α-synuclein protofibrils/oligomers (FIG. 10).

The specific examples and embodiments described herein are exemplary only in nature and are not intended to be limiting of the invention defined by the claims. Further embodiments and examples, and advantages thereof, will be apparent to one of ordinary skill in the art in view of this specification and are within the scope of the claimed invention.

REFERENCES

Bieschke, J., et al. 2006. Small molecule oxidation products trigger disease-associated protein misfolding. Acc Chem Res 39, 611-619.

Chartier-Harlin, M C., et al. 2004. Alpha-synuclein locus duplication as a cause of familial Parkinson's disease. Lancet 1, 364, 1167-9.

Conway, K., et al., 2000. Acceleration of oligomerization, not fibrillization, is a shared property of both α-synuclein mutations linked to early-onset Parkinson's disease: Implications for pathogenesis and therapy. Proc Natl Acad Sci USA 97, 571-576.

El-Agnaf, O. M., et al., 2006. Detection of oligomeric forms of α-synuclein protein in human plasma as a potential biomarker for Parkinson's disease. Faseb J 20, 419-425.

Hansen, L, et al., 1990. The Lewy body variant of Alzheimer's disease. A clinical and pathologic entity. Neurology 40, 1-8.

Jeffries, R. 2009 Glycosylation as a strategy to improve antibody-based therepeutics Nature 8, 226-234.

Klucken, J., et al., 2006. Clinical and biochemical correlates of insoluble α-synuclein in dementia with Lewy bodies. Acta Neuropathol (Berl) 111, 101-108.

Kruger, R. et al, 1998. Ala30Pro mutation in the gene encoding a α-synuclein in Parkinson's disease. Nat Genet. 18, 106-108.

Näsström, T et al., 2009. The lipid peroxidation metabolite 4-oxo-2-nonenal cross-links α-synuclein causing rapid formation of stable oligomers. Biochem Biophys Res Commun 378, 872-876.

Polymeropoulos, M. H., et al., 1997. Mutation in the a-Synuclein Gene Identified in Families with Parkinson's Disease. Science 276, 2045-47.

Qin, Z., et al., 2007. Effect of 4-hydroxy-2-nonenal modification on α-synuclein aggregation. J Biol Chem 282, 5862-5870.

Shamoto-Nagai, M., et al., 2007. In parkinsonian substantia nigra, α-synuclein is modified by acrolein, a lipid-peroxidation product, and accumulates in the dopamine neurons with inhibition of proteasome activity. J Neural Transm 144, 1559-1567.

Singleton, AB., et al., 2003. alpha-Synuclein locus triplication causes Parkinson's disease. Science 302:841.

Tsigelny, IF., et al., "Mechanism of hybrid oligomer formation in the pathogenesis of combined Alzheimer's and Parkinson's Diseases."

PloS ONE September 2008, vol 3 issue 9, e3135, p 1-15 www.plosone.org

Yoritaka, A., et al., 1996 Immunohistochemical detection of 4-hydroxynonenal protein adducts in Parkinson disease. Proc Natl Acad Sci USA 93, 2696-2701.

Zarranz, J., et al., 2004. The new mutation, E46K, of α-synuclein causes Parkinson and Lewy body dementia. Ann Neurol. 55, 164-173.

The invention claimed is:

1. An antibody, produced from a stabilized soluble α-synuclein oligomer and capable of binding a stabilized soluble α-synuclein oligomer, the stabilized soluble α-synuclein oligomer having a lower formation rate to a non-soluble aggregated form than a non-stabilized soluble oligomer of the α-synuclein, wherein the antibody has been collected from a non-human animal to which stabilized soluble α-synuclein oligomer had been administered.

2. The antibody according to claim 1, wherein the stabilized soluble α-synuclein oligomer comprises a stabilized soluble α-synuclein protofibril.

3. An antibody composition, comprising an antibody according to claim 1 and one or more excipients selected from the group consisting of antibacterial agents, adjuvants, buffers, salts, pH-regulators, detergents, and any combination thereof, that are pharmaceutically acceptable for human or veterinary use.

4. A method of detecting soluble α-synuclein in vitro, comprising adding the antibody according to claim 1 to a biological sample comprising or suspected of comprising soluble α-synuclein; and detecting and measuring a concentration of any complex formed between the antibody and soluble α-synuclein.

5. The antibody according to claim 1, wherein the antibody is monoclonal.

6. The antibody according to claim 1, wherein the antibody is humanized, or modified to reduce antigenicity in humans.

7. The antibody according to claim 1, wherein the antibody is of IgG1 or IgG4 subclass.

8. The antibody according to claim 1, wherein the stabilized soluble α-synuclein oligomer comprises a soluble α-synuclein oligomer modified with 1-α-hydroxy-secosterol.

9. The antibody according to claim 1, wherein the stabilized soluble α-synuclein oligomer comprises a soluble α-synuclein oligomer cross-linked with at least one protein cross-linking agent selected from the group consisting of disuccinimidyl tartrate, bis-sulfosuccinimidyl suberimidate and 3,3-dithiobis-sulfosuccinimidyl propionate, and any combination thereof.

10. The antibody according to claim 1, wherein the α-synuclein oligomer comprises wild type α-synuclein (SEQ ID NO: 1), wild type α-synuclein in which one or more Ser and/or Ala amino acids have been replaced with Cys via site-directed mutagenesis, a mutant selected from the group consisting of A30P (SEQ ID NO: 2), E46K (SEQ ID NO: 3) and A53T (SEQ ID NO: 4), or any combination thereof.

11. The antibody according to claim 1, wherein the antibody is capable of binding wild type soluble α-synuclein oligomers.

12. The antibody according to claim 1, wherein the antibody has higher binding strength to soluble α-synuclein oligomers as compared with binding strength to α-synuclein monomers.

13. The antibody according to claim 1, wherein the ratio of the $IC_{50}$ binding strength of the antibody to soluble α-synuclein protofibrils to the $IC_{50}$ binding strength of the antibody to α-synuclein monomers is in the range of about 1:50 to 1:2000.

14. The antibody according to claim 1, wherein the antibody has higher binding strength to soluble α-synuclein oligomers as compared with binding strength to insoluble α-synuclein fibrils.

15. The antibody according to claim 1, wherein the ratio of the $IC_{50}$ binding strength of the antibody to soluble α-synuclein protofibrils to the $IC_{50}$ binding strength of the antibody to insoluble α-synuclein fibrils is in the range of about 1:2 to 1:2000.

16. The antibody according to claim 1, wherein the stabilized soluble α-synuclein oligomer comprises a soluble α-synuclein oligomer modified with a hydrophobic organic agent.

17. The antibody according to claim 16, wherein the hydrophobic organic agent comprises an aldehyde.

18. The antibody according to claim 16, wherein the hydrophobic organic agent is selected from the group consisting of 4-hydroxy-2-nonenal, malondialdehyde, 4-oxo-2-nonenal, and acrolein, and any combination thereof.

19. The antibody according to claim 16, wherein the hydrophobic organic agent comprises a saturated, unsaturated, or polyunsaturated fatty acid, or a derivative or combination thereof.

20. The antibody according to claim 16, wherein the hydrophobic organic agent comprises a non-ionic detergent or a zwitterionic detergent, or any combination thereof.

21. The antibody according to claim 16, wherein the hydrophobic organic agent comprises at least one compound selected from the group consisting of triglycerides, phospholipids, sphingolipids, gangliosides, cholesterol, cholesterol-esters, long chain alcohols, and any combination thereof.

22. The antibody according to claim 16, wherein the hydrophobic organic agent comprises a bile acid derivative selected from the group consisting of deoxycholate, cholate and taurocholate, and any combination thereof.

23. An antibody, produced from a stabilized soluble α-synuclein oligomer and capable of binding a stabilized soluble α-synuclein oligomer, the stabilized soluble α-synuclein oligomer having a lower formation rate to a non-soluble aggregated form than a non-stabilized soluble oligomer of the α-synuclein, wherein the antibody has been produced by hybridoma technology, phage display, ribosome display, mammalian cell display or bacterial display.

24. The antibody according to claim 23, wherein the stabilized soluble α-synuclein oligomer comprises a stabilized soluble α-synuclein protofibril.

25. An antibody composition, comprising an antibody according to claim 23 and one or more excipients selected from the group consisting of antibacterial agents, adjuvants, buffers, salts, pH-regulators, detergents, and any combination thereof, that are pharmaceutically acceptable for human or veterinary use.

26. A method of detecting soluble a-synuclein in vitro, comprising adding the antibody according to claim 23 to a biological sample comprising or suspected of comprising soluble α-synuclein; and detecting and measuring a concentration of any complex formed between the antibody and soluble α-synuclein.

27. The antibody according to claim 23, wherein the antibody is monoclonal.

28. The antibody according to claim 23, wherein the antibody is humanized, or modified to reduce antigenicity in humans.

29. The antibody according to claim 23, wherein the antibody is of IgG1 or IgG4 subclass.

30. The antibody according to claim 23, wherein the stabilized soluble α-synuclein oligomer comprises a soluble α-synuclein oligomer modified with 1-α-hydroxy-secosterol.

31. The antibody according to claim 23, wherein the stabilized soluble α-synuclein oligomer comprises a soluble α-synuclein oligomer cross-linked with at least one protein cross-linking agent selected from the group consisting of disuccinimidyl tartrate, bis-sulfosuccinimidyl suberimidate and 3,3-dithiobis-sulfosuccinimidyl propionate, and any combination thereof.

32. The antibody according to claim 23, wherein the α-synuclein oligomer comprises wild type α-synuclein (SEQ ID NO: 1), wild type α-synuclein in which one or more Ser and/or Ala amino acids have been replaced with Cys via site-directed mutagenesis, a mutant selected from the group consisting of A30(SEQ ID NO: 2), E46K (SEQ ID NO: 3) and A53T (SEQ ID NO: 4), or any combination thereof.

33. The antibody according to claim 23, wherein the antibody is capable of binding wild type soluble α-synuclein oligomers.

34. The antibody according to claim 23, wherein the antibody has higher binding strength to soluble α-synuclein oligomers as compared with binding strength to α-synuclein monomers.

35. The antibody according to claim 23, wherein the ratio of the $IC_{50}$ binding strength of the antibody to soluble α-synuclein protofibrils to the $IC_{50}$ binding strength of the antibody to α-synuclein monomers is in the range of about 1:50 to 1:2000.

36. The antibody according to claim 23, wherein the antibody has higher binding strength to soluble α-synuclein oligomers as compared with binding strength to insoluble α-synuclein fibrils.

37. The antibody according to claim 23, wherein the ratio of the $IC_{50}$ binding strength of the antibody to soluble α-synuclein protofibrils to the $IC_{50}$ binding strength of the antibody to insoluble α-synuclein fibrils is in the range of about 1:2 to 1:2000.

38. The antibody according to claim 23, wherein the stabilized soluble α-synuclein oligomer comprises a soluble α-synuclein oligomer modified with a hydrophobic organic agent.

39. The antibody according to claim 38, wherein the hydrophobic organic agent comprises an aldehyde.

40. The antibody according to claim 38, wherein the hydrophobic organic agent is selected from the group consisting of 4-hydroxy-2-nonenal, malondialdehyde, 4-oxo-2-nonenal, and acrolein, and any combination thereof.

41. The antibody according to claim 38, wherein the hydrophobic organic agent comprises a saturated, unsaturated, or polyunsaturated fatty acid, or a derivative or combination thereof.

42. The antibody according to claim 38, wherein the hydrophobic organic agent comprises a non-ionic detergent or a zwitterionic detergent, or any combination thereof.

43. The antibody according to claim 38, wherein the hydrophobic organic agent comprises at least one compound selected from the group consisting of triglycerides, phospholipids, sphingolipids, gangliosides, cholesterol, cholesterol-esters, long chain alcohols, and any combination thereof.

44. The antibody according to claim 38, wherein the hydrophobic organic agent comprises a bile acid derivative selected from the group consisting of deoxycholate, cholate and taurocholate, and any combination thereof.

* * * * *

```
SEQUENCE LISTING

<160> NUMBER OF SEQ ID NOS: 8

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125
```

```
Ser Glu Glu Gly Tyr Gln Asp Tyr Glu Pro Glu Ala
    130                 135                 140

<210> SEQ ID NO 2
<211> LENGTH: 140
<212> TYPE: PRT
<213> ORGANISM: Homo sapiens

<400> SEQUENCE: 2

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Pro Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 3
<211> LENGTH: 140
<212> TYPE: PRT
<213> ORGANISM: Homo sapiens

<400> SEQUENCE: 3

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Lys Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 4
<211> LENGTH: 140
<212> TYPE: PRT
<213> ORGANISM: Homo sapiens
```

<400> SEQUENCE: 4

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Thr Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

<210> SEQ ID NO 5
<211> LENGTH: 140
<212> TYPE: PRT
<213> ORGANISM: Homo sapiens

<400> SEQUENCE: 5

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Pro Gly Lys
            20                  25                  30

Thr Lys Glu Gly Val Leu Tyr Val Gly Ser Lys Thr Lys Lys Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

<210> SEQ ID NO 6
<211> LENGTH: 140
<212> TYPE: PRT
<213> ORGANISM: Homo sapiens

<400> SEQUENCE: 6

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Pro Gly Lys
            20                  25                  30

```
Thr Lys Glu Gly Val Leu Tyr Val Gly Ser Lys Thr Lys Glu Gly Val
            35                  40                  45

Val His Gly Val Thr Thr Val Ala Glu Lys Thr Lys Glu Gln Val Thr
 50                      55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

<210> SEQ ID NO 7
<211> LENGTH: 140
<212> TYPE: PRT
<213> ORGANISM: Homo sapiens

<400> SEQUENCE: 7

Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Gly Lys
                20                  25                  30

Thr Lys Glu Gly Val Leu Tyr Val Gly Ser Lys Thr Lys Lys Gly Val
            35                  40                  45

Val His Gly Val Thr Thr Val Ala Glu Lys Thr Lys Glu Gln Val Thr
 50                      55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

<210> SEQ ID NO 8
<211> LENGTH: 140
<212> TYPE: PRT
<213> ORGANISM: Homo sapiens

<400> SEQUENCE: 8

Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Pro Gly Lys
                20                  25                  30

Thr Lys Glu Gly Val Leu Tyr Val Gly Ser Lys Thr Lys Lys Gly Val
            35                  40                  45

Val His Gly Val Thr Thr Val Ala Glu Lys Thr Lys Glu Gln Val Thr
 50                      55                  60

Asn Val Gly Gly Ala Val Val Thr Gly Val Thr Ala Val Ala Gln Lys
 65                  70                  75                  80
```

```
Thr Val Glu Gly Ala Gly Ser Ile Ala Ala Ala Thr Gly Phe Val Lys
                85              90              95

Lys Asp Gln Leu Gly Lys Asn Glu Glu Gly Ala Pro Gln Glu Gly Ile
            100             105             110

Leu Glu Asp Met Pro Val Asp Pro Asp Asn Glu Ala Tyr Glu Met Pro
        115             120             125

Ser Glu Glu Gly Tyr Gln Asp Tyr Glu Pro Glu Ala
    130             135             140
```